United States Patent [19]

Glenney

[11] Patent Number: 5,108,707
[45] Date of Patent: Apr. 28, 1992

[54] METHOD AND APPARATUS FOR REACTING AND WASHING MULTIPLE SAMPLE FILTERS

[76] Inventor: John Glenney, 3316 Bellafonte Dr., Lexington, Ky. 40502

[21] Appl. No.: 534,024

[22] Filed: Jun. 4, 1990

[51] Int. Cl.$^5$ .................. B01L 11/00; C12M 1/16
[52] U.S. Cl. ...................... 422/99; 422/102; 422/292; 435/299
[58] Field of Search .............. 422/58, 99, 102, 292, 422/300, 301; 435/299, 300, 301, 316; 134/135, 192, 196, 197; 354/340, 344, 337, 335, 326, 331

[56] References Cited

U.S. PATENT DOCUMENTS

| | | | |
|---|---|---|---|
| 1,631,045 | 5/1927 | Macon | 134/192 X |
| 2,566,819 | 9/1959 | Baltsois | 134/135 |
| 3,139,097 | 6/1964 | Hungerford et al. | 134/197 X |
| 3,199,431 | 8/1965 | Hill | 354/344 |
| 3,779,148 | 12/1973 | Hill | 354/344 |
| 4,247,298 | 1/1981 | Rippie | 422/101 X |
| 4,332,455 | 6/1982 | Stettner | 354/335 X |
| 4,622,076 | 11/1986 | Ling | 422/102 X |
| 4,787,988 | 11/1988 | Bertoncini et al. | 422/101 X |

FOREIGN PATENT DOCUMENTS

| | | | |
|---|---|---|---|
| 0022758 | 4/1891 | United Kingdom | 354/337 |
| 0017722 | 4/1903 | United Kingdom | 354/337 |

Primary Examiner—Robert J. Warden
Assistant Examiner—Stephanie Blythe
Attorney, Agent, or Firm—Donald L. Cox; Scott R. Cox

[57] ABSTRACT

A method and apparatus is described herein which allows filters, to which bacterial or mammalian cell samples have been absorbed, to be reacted sequentially by various scientific means and to be washed between analyses. The filters are placed between interconnected parallel separation plates on the filter agitator. The filter holder is lowered into a reaction container that contains reaction or wash solutions. The filter holder is raised or lowered in the reaction container by physical or mechanical means. The reaction container is covered by a lid which prevents splashing and contamination of the solution or filters. Solutions are added by means of a fill tube located in the lid and emptied by means of a drain in the reaction container. Once the sequential analysis is complete, gene product on the sample filters is detected by an appropriate method.

4 Claims, 4 Drawing Sheets

METHOD AND APPARATUS FOR REACTING AND WASHING MULTIPLE SAMPLE FILTERS

BACKGROUND OF INVENTION

1. Field of Invention

This invention relates to a method and apparatus that allows filters with absorbed bacterial or mammalian cell samples to be analyzed for specific genes and gene products. More particularly this invention relates to a device that allows the experimenter to perform sequential operations or analysis on one or a large number of filters to identify bacterial or mammalian cells which contain specific genes.

2. Prior Art

Protein-encoding DNA of different organisms can be inserted into various strains of bacteria, creating what is commonly known as a cDNA Library. Generally, enzymes duplicate the mRNA of an organism into thousands of individual complimentary DNA fragments. These DNA fragments are then packaged in certain phages, which, by well known biomechanisms, insert the DNA segments into the genome of a particular strain of bacteria.

The bacterial colonies are cultivated on agar plates. The bacterial colony which contains the gene of interest is detected by a variation of replica plating. Nitrocellulose filters are applied to the surface of the colonized agar plates. Bacteria adhere to the nitrocellulose filters or gene products secreted by bacteria are absorbed into the filter. Reference marks on the filter paper and the plate make it possible to run various assays on the filter paper and later identify the colony, if any, which harbors the particular gene of interest. As thousands to literally millions of individual bacterial colonies are cultivated, each containing a small fragment of the specimen genome, ten to one hundred of agar plates may be needed to grow the colonies. Consequently, this same number of filters would be used to sample the colonies on each agar plate.

The colony containing the gene of interest can be identified by radiolabelled DNA or mRNA probes. The gene product can be traced by using monoclonal or polyclonal antibodies coupled with enzymatic or fluorescent tags, or by means of enzymatic assays. Other protein to protein or protein to DNA interactions can be detected in a similar way.

A new technique which uses phage technology to introduce complementary DNA for antibody heavy and light chain fragments into strains of E.Coli will substantially increase the need for rapid sequential analysis of large numbers of filters. The bacteria or phage that produce antibody fragments are cultured on agar plates. A filter is laid on top of the agar plate to absorb the antibody fragments. These filters are then tested against solutions containing labelled antigen. This technique is essentially the reverse of the method previously described.

Whatever detection method is chosen, each one of the sample filters must be subjected to the same assay method under controlled conditions. These tests require that the filters be agitated in various solutions which contain the reagents for the assay and then washed in buffer solutions.

One method of agitating filters in solution is to place the filters in a heat sealed or lock plastic bag of the type frequently used in kitchens. A solution is added to the bag, the bag is sealed, and the filters are agitated inside the bag by hand or simply allowed to soak.

This method has several limitations. The most severe of which is the uneven application of the antibody or reagent solution to the filter surface and diffusion through the filter. This problem is caused by air bubbles in the plastic bag, contact between the sides of the bag and the filter surface, contact between the surfaces of two or more filters in the bag or limited diffusion through a stack of filters. Effective washing of the filters with buffers and other solutions is similarly retarded.

Other disadvantages are also present. The filters are more likely to tear or otherwise be damaged during the agitation process. Bubbles can form and be trapped between filters. The size of the bag limits the number of filters that can be reacted or washed at one time. It is often difficult to control various experimental parameters using a plastic bag such as reaction time, temperature and reagent concentration. Further, the plastic bag method results in an unacceptable number of false positive reactions.

In a second method, the filters are placed in glass crystallizing dishes which contain the reaction or wash solution. The dishes are covered with a lid or a plastic wrap. The dish is then placed on a rotating platform which agitates the filter inside the dish. The disadvantages of this technique are myriad. If several filters are placed in a crystallizing dish, they must frequently be separated because of a tendency to stick to one another and to the sides of the dish. In addition, a separate crystallizing plate must be used for each step of the reaction or wash. During the transfer from one dish to the next, the filter may become contaminated or torn and wash or incubation liquid is easily spilled. Evaporation of the reaction or wash solution may adversely effect the concentration of the reactants. Finally, with a sequential analysis using several such dishes, it is difficult to control such variables as time, temperature and concentration when transferring the filter from dish to dish.

A device described by Larry W. Cohen in Bio Techniques, Vol. 8, No. 4 (1990) employs two plexiglass boxes to apply solutions containing radiolabelled probes to filters. One box is filled with a radioactive solution. A smaller box has contiguous groves cut in two sides and the bottom. Hybridization filters are placed in the grooves. The box holding the filters is then lowered into the box containing the solution. When the reaction is finished, the smaller box is raised and drained.

There are several disadvantages connected with this device. First, the groove system provides insufficient support for filters immersed in solution causing the filters to collapse against each other and the wall of the vessel when the filter box is removed. Because there is no method of draining the larger box, the filter box must be removed and the larger box filled and drained by hand. This makes it difficult to control parameters of temperature and concentration. In addition, the filters may be contaminated or dry out when exposed to air. Further, in order to do a series of sequential analyses, several boxes would have to be used, each containing a different reactor or wash solution. Although agitation would facilitate the reaction and washing of the filters, no means for agitating the filters was apparent.

Other patents describe devices and processes for sequential analysis of bacterial samples. U.S. Pat. No. 4,237,096 describes a device which is a series of reaction chambers. Liquid containing whole bacteria, lysed bacteria or secreted gene products is introduced into the chamber by a gravity feed channel. The liquid flows into each chamber by means of a ball valve. When the desired amount of sample is in each chamber, a reagent is added to the sample chambers. Plainly, the usefulness of this device is limited to testing of samples in liquid media. Further, the analyses must produce color change reaction to be detectable. Finally, because the samples cannot be washed, probes such as labelled monoclonal or polyclonal antibodies could not be used.

U.S. Pat. No. 4,632,901 describes a method and apparatus for doing immunoassays. The device has two members the first of which is a filter with a monoclonal antibody bound to it. A second member is made up of an absorbent material. A liquid sample is poured onto the test filter through a funnel device which houses the filter. The absorbent material facilitates the flow of liquid through the filter. Antigens in the sample are bound to the antibody in the filter. Radio labelled antibody is added, followed by several washes. The filter is then tested for the presence of labelled antibody. The main disadvantage of this device is that only one filter can be tested at a time. Further, this process is not suitable for sequential analysis. Finally, reactions that require controlled parameters such as reactant concentration, temperature, and reaction time cannot be done with this device.

U.S. Pat. No. 4,673,638 describes a method for detecting microorganisms which produce a desired substance. A porous membrane of inert material is placed on top of the agar surface in a growth plate. Bacteria are grown on the membrane. Secreted substances pass through the membrane into the agar. The bacteria can also be lysed allowing non-secreted substances to run through the membrane into the agar. The membrane with the growing bacteria is lifted from the agar surface and stored appropriately. Reagents in the agar itself, or placed on the surface of the agar, react with the bacterial substrate and a reaction is observed in the agar. Although it is claimed that more colonies can be screened by this method it is clear that only one analysis can be run on each agar plate. In addition, it would not be practical to use radio or flourescene labelled probes because of background problems created by diffiusion of the probe solution into the agar.

Therefore, it is an object of this invention to provide a reaction-wash vessel for use with various sizes and types of filters.

It is another object of this invention to provide a reaction-wash vessel that allows individual filters to be easily inserted and removed.

It is another object of this invention to provide a reaction-wash vessel that allows up to 100 filters to be reacted and washed at one time.

It is still a further object of this invention to provide a reaction-wash vessel that allows filters to be agitated without adhering to the side of the apparatus or to other filters.

It is a still further object of this invention to provide a reaction-wash vessel that provides for uniform application of a reagent and/or wash solution to the surface of single or multiple filters.

It is still a further object of this invention to provide a reaction-wash vessel that allows multiple filters to be assayed under similar controlled conditions.

It is still a further object of this invention to provide a reaction-wash vessel in which several different analyses and washes can be done on sample filters in the same reaction-wash vessel.

It is still a further object of this invention to provide a reaction-wash vessel in which bubbles are hindered from forming and adhering to the surface of a filter during a reaction or wash.

It is still a further object of this invention to provide a means for precisely controlling the temperature of the reaction-wash vessel filter solution.

It is still a further object of this invention to provide a process for performing sequential analysis on multiple sample filters.

SUMMARY OF THE INVENTION

In accordance with the present invention there is provided a process for easily performing analyses which uses a simple apparatus being a reaction-wash vessel intended to be an improved means of reacting and washing filter samples. The device is comprised of a reaction-wash container. Inside the reaction-wash container is a filter holder. The filter holder consists of two to many plates arranged vertically and in parallel attached to a handle. The handle is used to raise and lower the filter holder inside the reaction-wash container. A lid fits over the top of the device to prevent the reaction and/or wash solutions from splashing and spilling. The reaction-wash container ca be filled by means of a conduit located in the lid of the device. The reaction-wash container can be emptied by means of a drain that is attached to the bottom of the reaction-wash container. Thus, the system is essentially closed.

In use, the drain is plugged so that the reaction-wash container can be filled through the lid conduit with a reagent solution or solution containing antibodies, protein, DNA, RNA or other probes. Nitrocellulose, nylon, PLDF or other filters are placed between the vertical parallel filter plates located on the filter holder. These plates hold the filters in an upright position. The filter holder is then lowered into the container until the filters are completely submerged in the reaction or wash solution. The filter holder is raised and lowered by means of an attached handle. A lid is placed on the vessel to prevent splashing or spilling of solutions in the vessel. This lid also prevents evaporation and contamination of the solutions while in the vessel. When the sequential analysis is complete the gene products on the sample filters are detected by the appropriate means.

BRIEF DESCRIPTION OF THE DRAWINGS

FIG. 7 is a front perspectsive view of the device enclosed in a water jacket.

FIG. 8 is a view looking down on the device inside the water jacket.

DESCRIPTION OF THE PREFERRED EMBODIMENT

Figure 1:
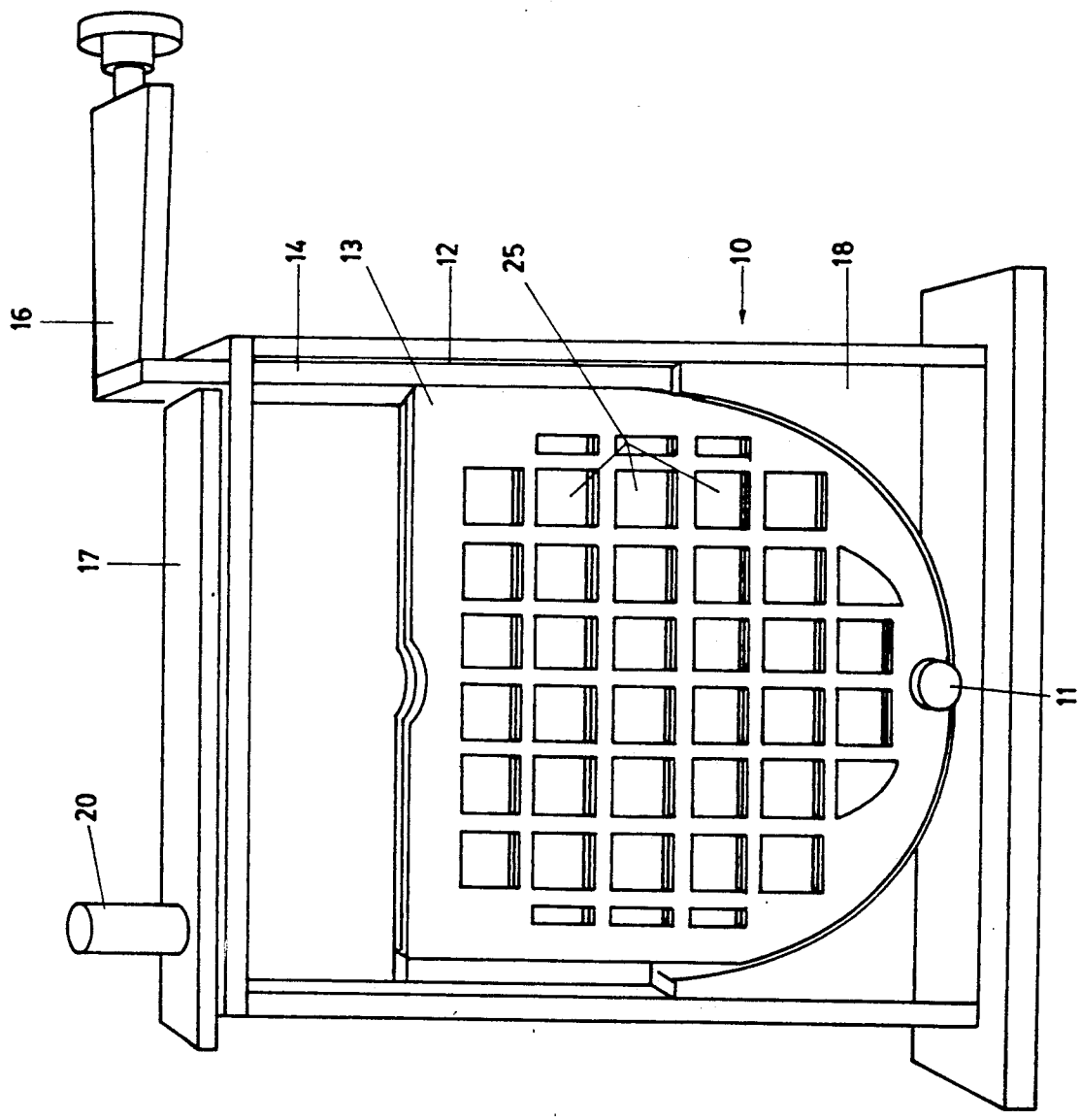
FIG. 1 is a front perspective view showing all the components of the reaction-wash vessel.

As shown in FIG. 1, the reaction-wash container (10) is comprised of four sides and a base constructed in such a manner as to permit the filter holder (12) to move inside the container without hindrance. In a preferred embodiment the bottom of the inside of the reaction-wash container (10) is a concave shaped filter holder rest (18) which corresponds in size to the shape of the filter holder (12) to be placed within the reaction-wash container (10). This concave shape allows for more economical analyses because it decreases the amount of solution necessary to fill the reaction vessel to the point where the filters are submerged. Further, this feature facilitates reactions and washes by increasing fluid circulation between the filters.

Figure 2:
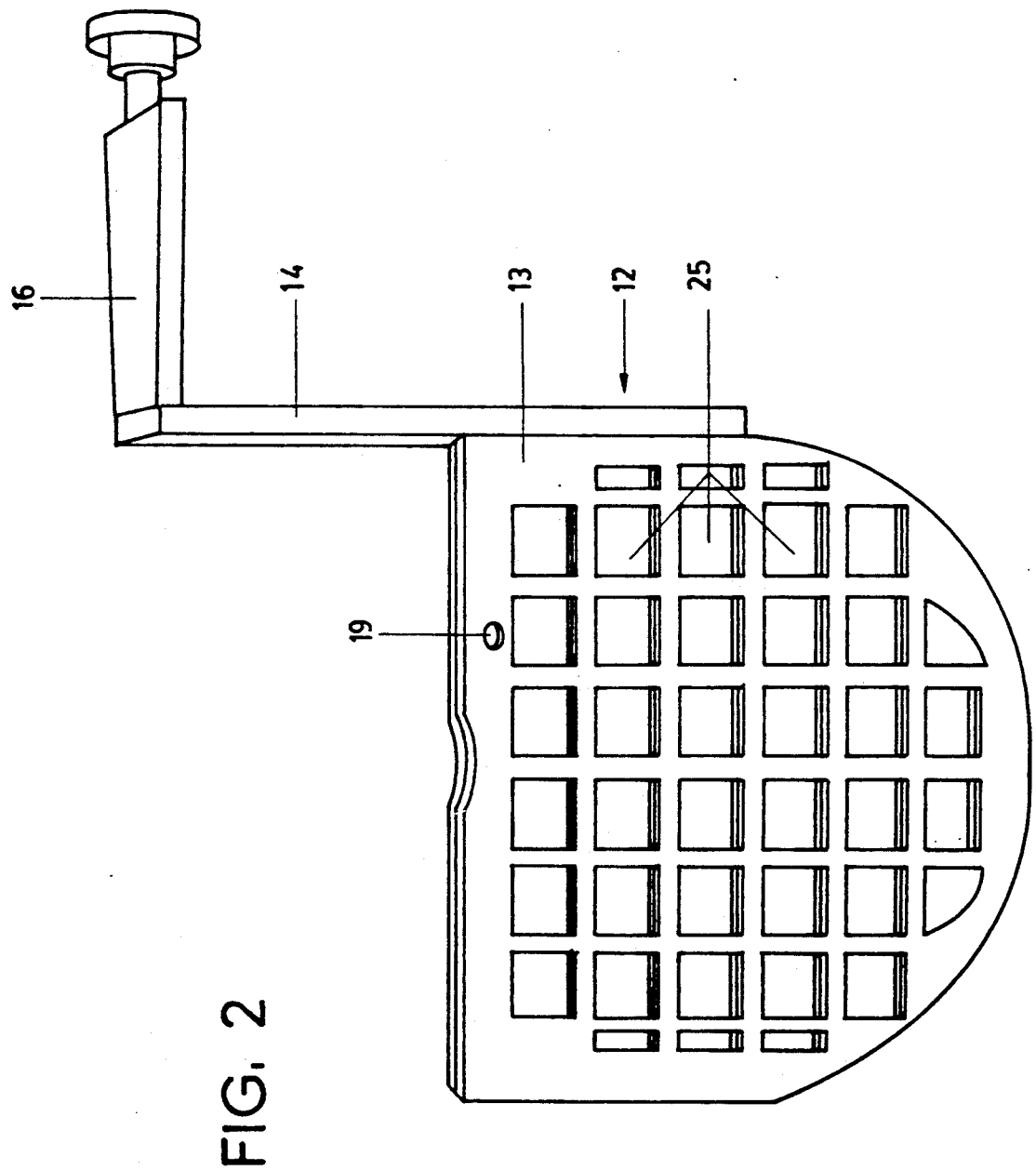
FIG. 2 is a front view of the filter holder.
Figure 3:
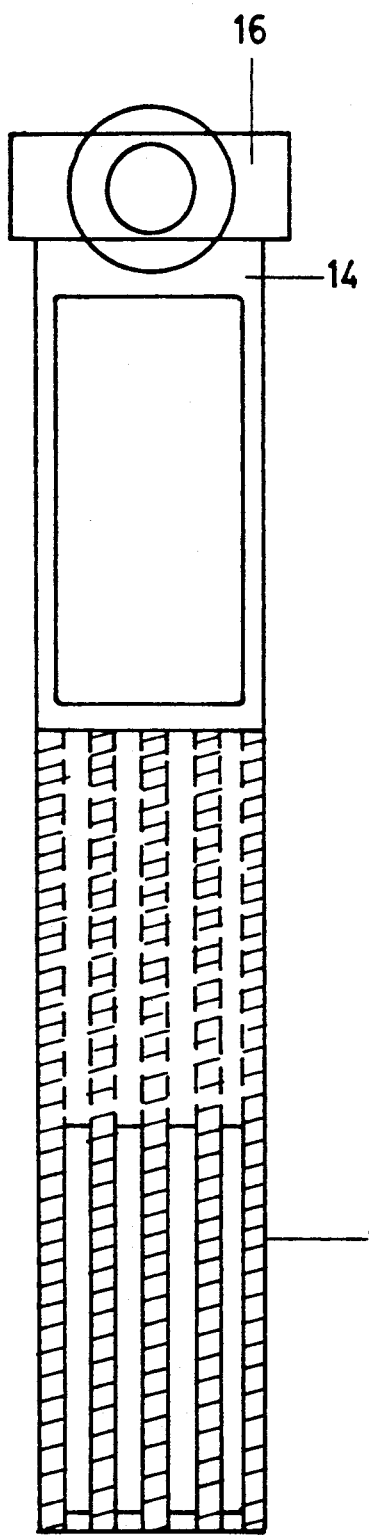
FIG. 3 is a right side view of the filter holder.

FIG. 2 shows the filter holder, (12). The filter holder (12) is comprised of vertical filter separation plates (13) which are connected in parallel to one another as demonstrated in FIGS. 3 and 4. A side arm (14) is attached to the plates to allow them to be raised and lowered in the reaction-wash container (10). In a preferred embodiment the side arm can be attached to a power source by a coupling arm (16) so that the filter holder (12) can be raised and lowered mechanically. As shown in FIG. 2, the preferred embodiment contemplates a filter holder (12) with vertical parallel filter separation plates (13) that approximate the shape and size of a rounded filter of at least the diameter of the largest filter used in such assays. The convex shape of the filter holder (12), in a preferred embodiment, corresponds to the concavity in the reaction-wash container (10) of FIG. 1. In a more preferred embodiment there is a guide hole (19) in appropriate places in each of the parallel filter separation plates (13) to secure filters of different sizes between the plates. Once filters are placed in between the plates, a pin is placed into the guide hole appropriate for the size of the filter. The pin prevents the filters from floating out of the slots between the filter separation plates (13) as the filter holder (12) is being raised and lowered in a solution. In a preferred embodiment the guide hole (19) is drilled in an asymmetric location that allows the filters to rotate a they rub against the pin placed in the guide hole (19) as the filter holder (12) is raised and lowered. This facilitates the reaction or wash process.

Figure 5:
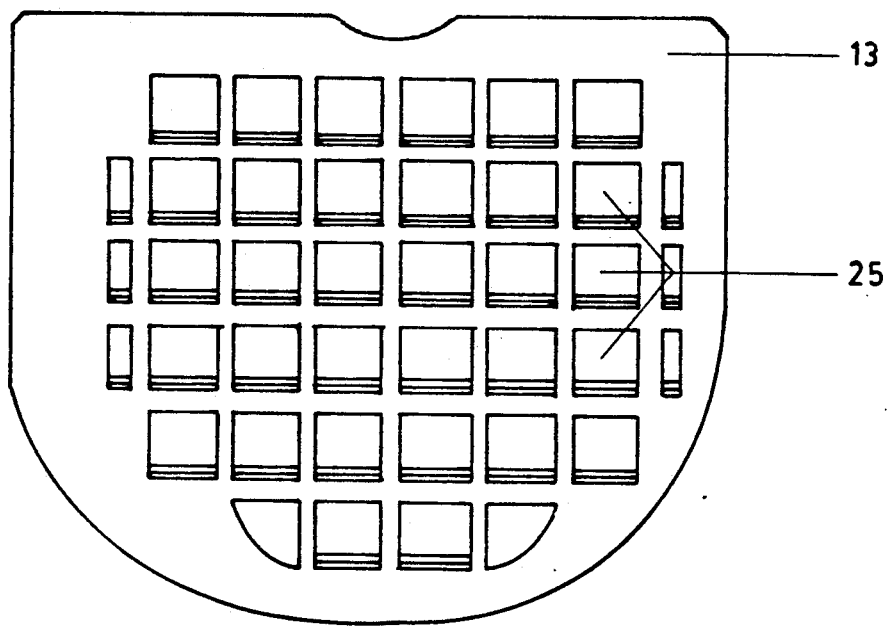
FIG. 5 is a front view of one of the filter separation plates.

FIG. 5 shows an individual filter separation plate (13). In a preferred embodiment the filter separation plates (13) have perforations (25) to allow free flow of fluid between the plates and filters said perforations being designed in such a way as to minimize the surface area of the plate that would contact the filter surface during the reaction wash process. In a more preferred embodiment the filter separation plates are shaped to closely approximate the size and contour of a filter.

Figure 6:
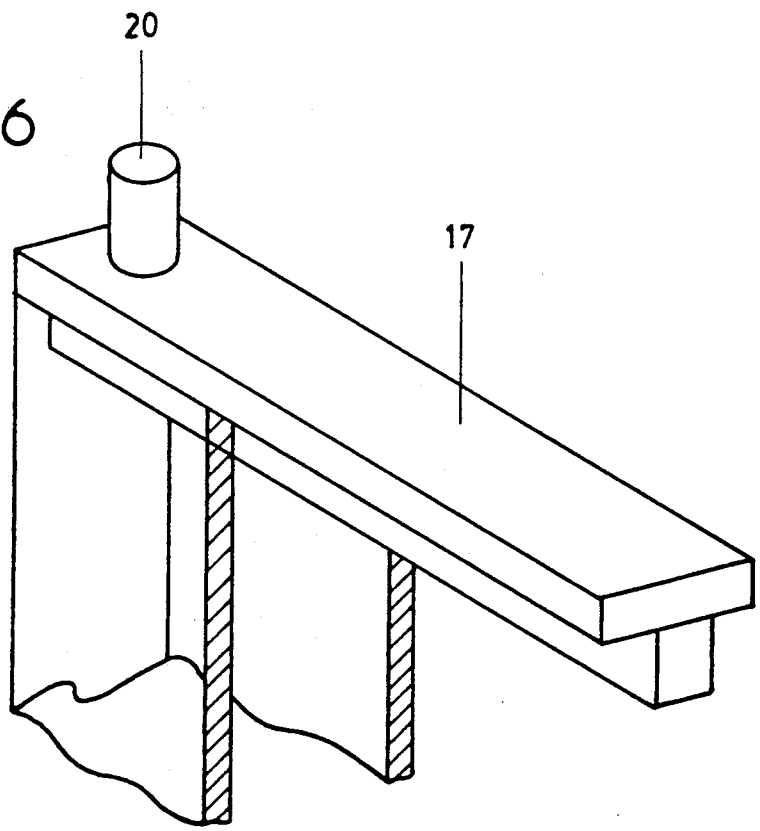
FIG. 6 is an elevated perspective view of the lid.

Once the filter holder (12) is placed in the reaction-wash container (10) a lid (17) is placed over the container itself to prevent splashing and evaporation of solutions in the container and to prevent contaminatants from entering the container. As shown in FIG. 6 the container lid (17) overlaps the reaction-wash container (10) opening. The container lid (17) covers the top of the reaction-wash container (10) while permitting the side arm (14) of the filter holder (12) to be moved without hindrance, as shown in FIG. 1. In a preferred embodiment a conduit (20) is attached to the container lid (17) by which reagent and wash solutions can be added to the container without removing the lid.

Figure 4:
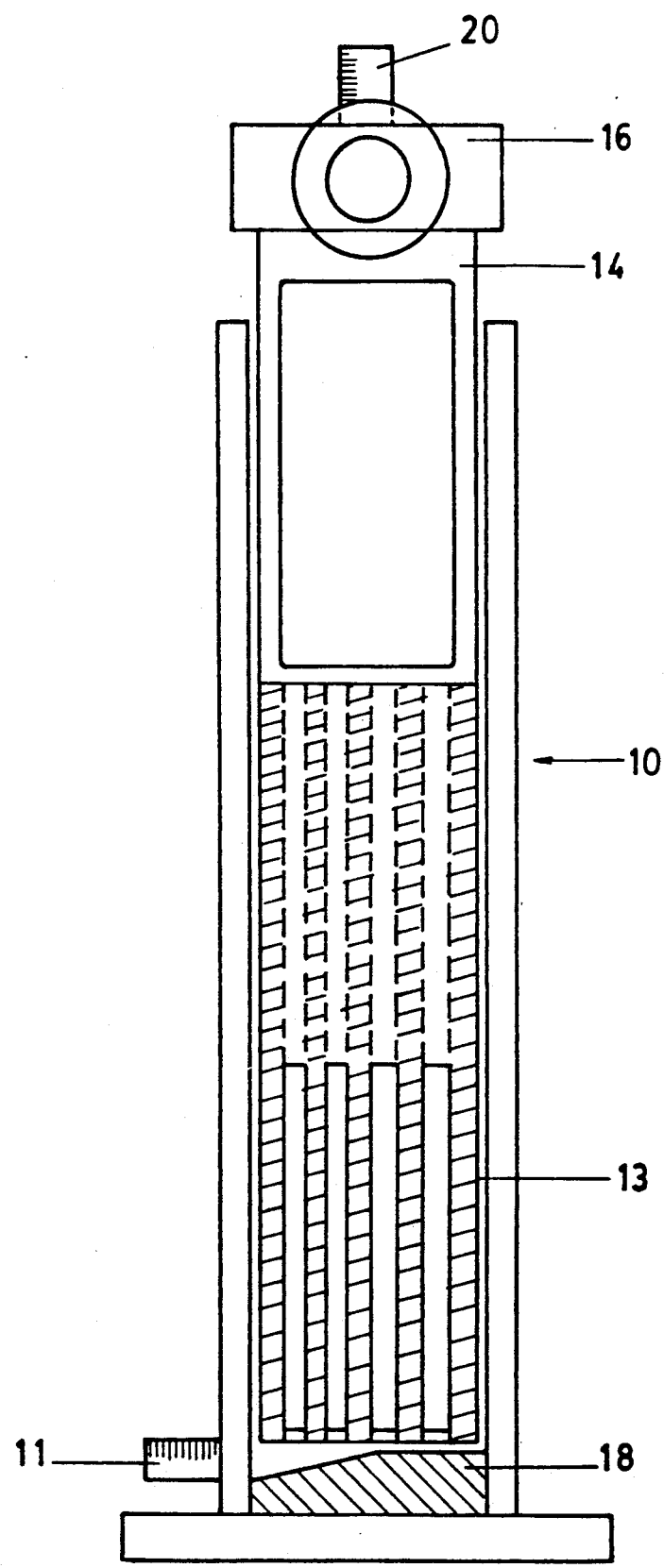
FIG. 4 is a cross-sectional view of the device.

In a preferred embodiment, the reaction-wash container (10) can be drained by means of a drain (11) which is attached to the reaction-wash container (10) as shown in FIGS. 1 and 4. This would permit different reaction solutions and multiple washes to be applied to the filters without putting the filters in different reaction vessels or exposing the filters to air. Thus, the reaction-wash container (10) is essentially a closed system.

To the extent not already indicated, it will also be understood by those of ordinary skill in the art that any of the various special embodiments herein described and may be further modified to incorporate features shown in any of the other specific embodiments, as described.

The invention in its broader aspects therefore is not limited to the specific embodiments herein shown and described but departures may be made therefrom within the scope of the accompanying claims, without departing from the principles of the invention and without sacrificing its chief advantages.

I claim:

1. A device for reacting or washing a plurality of filters simultaneously, said device comprised of:
   (a) a reaction was container;
   (b) a filter holder, comprising a plurality of parallel vertical, interconnected plates containing asymmetric guide holes, resting inside said container;
   (c) a pin for insertion into said guide holes; and
   (d) a lid, including a fill tube means, resting on said container.

2. A device for reacting or washing a plurality of filters simultaneously, said device comprised of:
   (a) a reaction wash container containing a drain means;
   (b) a filter holder, comprised of two parallel, vertical, interconnected plates containing asymmetric guide holes, wherein said plates are spaced at even intervals within the filter holder resting within said container;
   (c) a pin for insertion in said guide holes; and
   (d) a lid, including a fill tube means, resting on said container.

3. A device for reacting or washing a plurality of filters simultaneously, said device comprised of:
   (a) a reaction wash container comprised of sides and a bottom wherein the bottom of the reaction wash container is in a concave shape;
   (b) a drain means secured to the reaction wash container;
   (c) a filter holder, comprised of a plurality of substantially parallel, vertical, interconnected plates containing asymmetric guide holes, wherein said plates are spaced at even intervals, wherein said plates have a convex bottom, and wherein said holder rests inside said container;
   (d) a pin for insertion in said guide holes; and
   (e) a lid, including a fill tube means, resting on at least two sides of the container.

4. The device of claims 1, 2 or 3 wherein said interconnected plates are perforated.

* * * * *